United States Patent [19]

Weyer et al.

[11] 3,962,244

[45] June 8, 1976

[54] BENZENE SULFONYL UREAS

[75] Inventors: Rudi Weyer, Frankfurt am Main; Walter Aumuller, Kelkheim, Taunus; Ruth Heerdt, Mannheim; Volker Hitzel, Lorsbach, Taunus; Helmut Weber, Frankfurt am Main; Karl Muth, Kelkheim, Taunus, all of Germany

[73] Assignee: Hoechst Aktiengesellschaft, Frankfurt am Main, Germany

[22] Filed: July 17, 1974

[21] Appl. No.: 489,103

Related U.S. Application Data

[63] Continuation-in-part of Ser. No. 219,549, Jan. 20, 1972, abandoned, and Ser. No. 219,533, Jan. 20, 1972, abandoned.

[30] Foreign Application Priority Data

Dec. 13, 1971 Germany............................ 2161697
Jan. 23, 1971 Germany............................ 2103118

[52] U.S. Cl. .................... 260/256.5 R; 260/244 R; 260/248 AS; 424/248; 424/249; 425/251
[51] Int. Cl.² ...................................... C07D 239/72
[58] Field of Search ............................ 260/256.5 R

[56] References Cited
UNITED STATES PATENTS

| | | | |
|---|---|---|---|
| 3,274,194 | 9/1966 | Hayao............................... | 260/256.4 |
| 3,734,910 | 5/1973 | Ambrogia et al............... | 260/250 A |

*Primary Examiner*—Leonard Schenkman
*Attorney, Agent, or Firm*—Curtis, Morris & Safford

[57] ABSTRACT

Benzene sulfonyl ureas of the formula

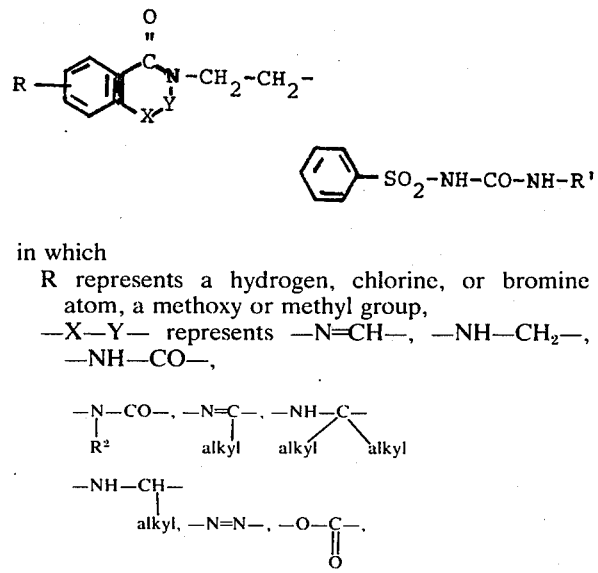

in which
R represents a hydrogen, chlorine, or bromine atom, a methoxy or methyl group,
—X—Y— represents —N=CH—, —NH—CH$_2$—, —NH—CO—, $$-\underset{\underset{R^2}{|}}{N}-CO-, \quad -\underset{\underset{alkyl}{|}}{N}=C-, \quad -NH-\underset{\underset{alkyl}{|}}{\overset{\underset{alkyl}{|}}{C}}-$$

$$-NH-\underset{\underset{alkyl}{|}}{CH}-, \quad -N=N-, \quad -O-\underset{\underset{O}{\|}}{C}-,$$

the alkyl herein containing from 1 to 4 carbon atoms,
R$^2$ represents an alkyl group having 1 to 4 carbon atoms
R$^1$ represents an alkyl group having from 3 to 6 carbon atoms, a cycloalkyl group having from 5 to 8 carbon atoms, 3-ethyl-cyclopentyl, methyl-cyclopentyl, dimethylcyclopentyl, 4-alkyl-cyclohexyl having from 1 to 3 carbon atoms in the alkyl group, cyclopentenyl, cyclohexenyl, cycloheptenyl, 4-chloro-cyclohexyl, 4,4-dimethylcyclohexyl, 3-methyl-cyclopentenyl, 4-methylcyclohexenyl, endoalkylene-cyclohexyl, endoalkylene-cyclohexenyl, bicyclo-(2.2.1) hept-2-en-7-yl, and their physiologically tolerable salts, useful for lowering blood sugar level in the treatment of *diabetes mellitus*.

13 Claims, No Drawings

BENZENE SULFONYL UREAS

This application is a continuation-in-part of application Ser. No. 219,549 and Ser. No. 219,533, both filed on Jan. 20, 1972, both now abandoned.

The present invention relates to sulfonyl ureas of the formula

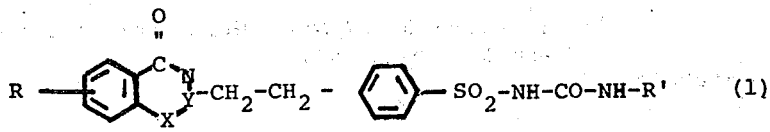   (1)

in which
R represents a hydrogen, chlorine, or bromine atom, a methoxy or methyl group
—X—Y— represents —N=CH—, —NH—CH₂—, —NH—CO—,

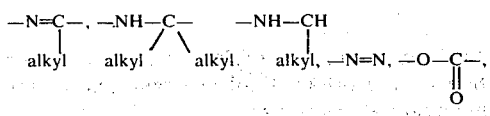

the alkyl herein containing from 1 to 4 carbon atoms,
R' represents an alkyl group having from 3 to 6 carbon atoms, a cycloalkyl group having from 5 to 8 carbon atoms, 3-ethylcyclopentyl, methyl-cyclopentyl, dimethylcyclopentyl, 4-alkylcyclohexyl having from 1 to 3 carbon atoms in the alkyl group, cyclopentenyl, cyclohexenyl, cycloheptenyl, 4-chlorocyclohexyl, 4,4-dimethylcyclohexyl, 3-methylcyclopentenyl, 4-methylcyclohexenyl, endoalkylene-cyclohexyl, endoalkylenecyclohexenyl, bicyclo- (2.2.1) hept-2-en-7-yl.

In addition, the present invention relates to sulfonyl ureas of the formula

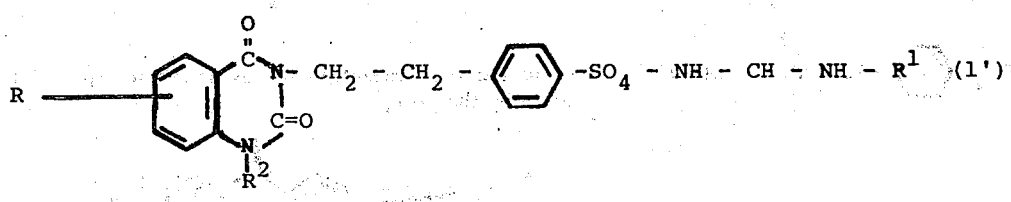

in which
R represents a hydrogen, chlorine, or bromine atom, a methoxy or methyl group,
R¹ represents an alkyl group having from 3 to 6 carbon atoms, a cycloalkyl group having from 5 to 8 carbon atoms, 3-ethylcyclopentyl, methyl-cyclopentyl, dimethylcyclopentyl, 4-alkyl-cyclohexyl having from 1 to 3 carbon atoms in the alkyl group, cyclopentenyl, cyclohexenyl, cycloheptenyl, 4-chloro-cyclohexyl, 4,4-dimethylcyclohexyl, 3-methylcyclopentenyl, 4-methylcyclohexenyl, bicyclo-(2.2.1) hept-2-en-7-yl, endoalkylene-cyclohexyl, endoalkylene-cyclohexenyl, having 1 or 2 endoalkylene-carbon atoms each.
R² represents an alkyl group having from 1 to 4 carbon atoms.

The compounds of the above formula have, in substance or in the form of their salts, a strong and long-lasting hypoglycemic action.

The present invention furthermore relates to a process for the manufacture of these sulfonyl ureas, which comprises introducing, optionally stepwise, into compounds containing the grouping of the formula (I)

   (I)

in which $n$, is zero or the integer 1 or 2, a radical of the formula (II)

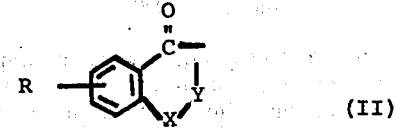   (II)

and a radical of the formula (III)
—CO—NH—R¹   (III)

radicals I and III being linked by means of a NH-group contained either in radical I or in radical III, oxidizing the reaction products, if necessary and optionally treating them with alkaline agents to obtain salts.

The above-mentioned radicals may, for example, be introduced a. by reacting benzenesulfonyl-isocyanates, benzenesulfonyl-carbamic acid esters, benzenesulfonyl-thiolcarbamic acid esters, benzenesulfonyl ureas, benzenesulfonyl-semicarbazides or benzenesulfonyl-semicarbazones which are substituted in 4-position by the group

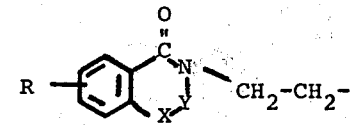

with an amine R' —NH₂ or salts thereof, or reacting sulfonamides of the formula

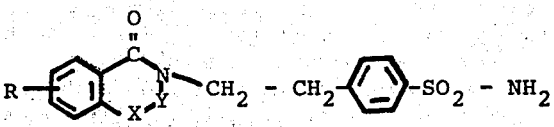

or the salts thereof with R'-substituted isocyanates, carbamic acid esters, thiolcarbamic acid esters, carbamic acid halides or ureas;

b. saponifying or hydrolyzing correspondingly substituted benzenesulfonyl-isourea ethers, benzenesulfonyl-isothiourea ethers, benzenesulfonyl-para-
banic acids or benzenesulfonyl-haloformic acid
amidines,
c. replacing in benzenesulfonyl-thioureas substituted
by the group

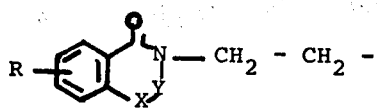

or in benzenesulfonyl-ureas or thioureas substituted by
the group

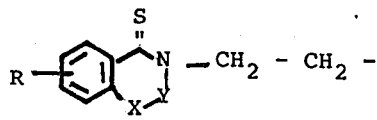

the sulphur atom or sulphur atoms by an oxygen
atom or oxygen atoms;
d. adding water to benzenesulfonyl-carbodiimides
correspondingly substituted by the group

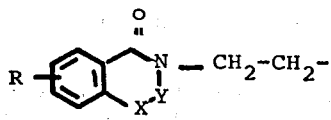

e. oxidizing correspondingly substituted benzenesul-
finyl-ureas or benzenesulfenyl ureas, or reacting
correspondingly substituted benzenesulphinic acid
halides; or in the presence of acid condensation
agents, even correspondingly substituted sulphinic
acids or alkali metal salts thereof with N — R' —
N'— hydroxy-ureas;
f. introducing, optionally stepwise, in benzenesulfo-
nyl-ureas of the formula

the radical

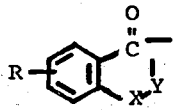

or
g. reacting correspondingly substituted benzenesulfo-
nyl-halides with R'-substituted ureas or alkali metal
salts thereof and optionally treating the reaction
products with alkaline agents to obtain salts.
This invention also relates to processes for the prepa-
ration of these benzenesulfonyl ureas which comprise
a. reacting benzenesulfonyl-isocyanates, benzenesul-
fonyl-carbamic acid esters, benzenesulfonyl-thiol-
carbamic acid esters, benzenesulfonyl ureas, ben-
zenesulfonyl-semicarbazides or benzenesulfonyl-
semicarbazones which are substituted in 4-position
by the group

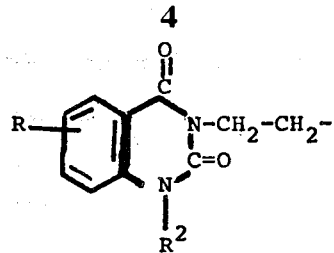

with an amine $R^1$-$NH_2$ or salts thereof, or reacting sul-
fonamides of the formula

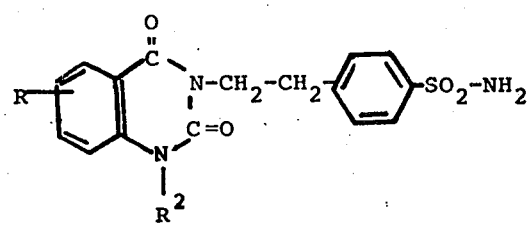

or the salts thereof with $R^1$-substituted isocyanates,
carbamic acid esters, thiolcarbamic acid esters, car-
bamic acid halides or ureas;
b. saponifying or hydrolyzing correspondingly substi-
tuted benzenesulfonyl-isourea ethers, benzenesul-
fonyl-isothiourea ethers, benzenesulfonyl-para-
banic acids or benzenesulfonyl-haloformic acid
amidines,
c. replacing in benzenesulfonyl-thioureas substituted
by the group

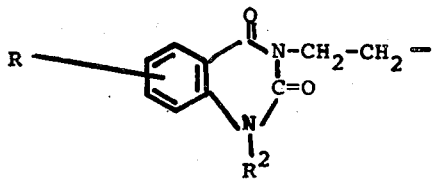

or in the benzenesulfonyl-ureas or -thioureas substi-
tuted by the group

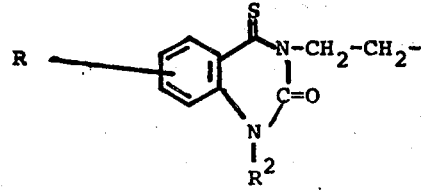

the sulphur atom or sulphur atoms by an oxygen
atom or oxygen atoms;
d. adding water to benzenesulfonyl-carbodiimides
correspondingly substituted by the group

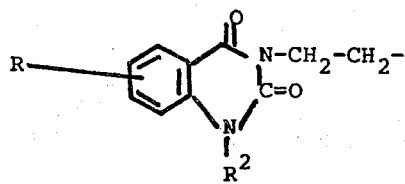

e. oxidizing correspondingly substituted benzenesul-
finyl-ureas or benzenesulfenyl ureas, f. introducing optionally stepwise, in benzenesulfonyl-ureas of the formula

the radical

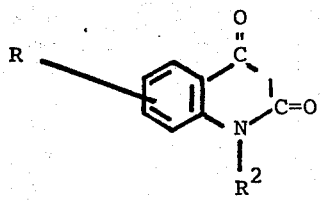

or g. reacting correspondingly substituted benzenesulfonyl-halides with R¹-substituted ureas or alkali metal salts thereof or reacting correspondingly substituted benzenesulfinic acid halides; or in the presence of acid condensation agents, correspondingly substituted-sulfinic acids or alkali metal salts thereof with N-R¹-N′-hydroxy-ureas; and, optionally treating the reaction products with alkaline agents to obtain salts.

The aforesaid benzenesulfonyl-carbamic acid esters or benzenesulfonyl-thiolcarbamic acid esters may carry in the alcoholic component an alkyl group or an aryl group or even a heterocyclic radical. Since this radical is split off during the reaction, its chemical constitution has no influence on the nature of the final product and may, therefore, be varied within wide limits. The same applies to N-R′-substituted carbamic acid esters and the corresponding thiocarbamic acid esters.

As carbamic acid halides, the chlorides are preferably used.

The benzenesulfonyl-ureas used as starting materials in the process of the present invention may be unsubstituted at the nitrogen atom of the urea molecule not joined to the sulfonyl group or may be mono- or especially di-substituted. Since these substituents are split off during the reaction with amines, their nature can be varied within wide limits. In addition to benzenesulfonyl-ureas which carry alkyl, aryl, acyl or heterocyclic substituents, there may also be used benzenesulfonyl-carbamoyl-imidazoles and similar compounds of bis(-benzenesulfonyl)-ureas which may carry at one of the nitrogen atoms a further substituent, for example, a methyl group. For example, such bis-(benzenesulfonyl)-ureas or N-benzenesulfonly —N′—acyl-ureas may be treated with R′-substituted amines and the salts thus obtained may be heated to elevated temperatures, especially to above 100°C.

Furthermore, it is possible to start from R′-substituted ureas or from R - substituted ureas which are mono- or, especially, di-substituted at the free nitrogen atom and to react them with benzenesulfonamides carrying the substituent

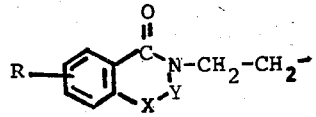

in 4-position, or the substituent

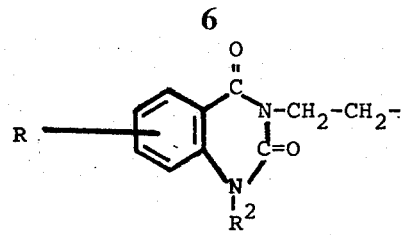

in 4-position.

As starting materials, there may be used, for example, N-cyclohexyl-urea, the corresponding N′-acetyl, N′-nitro-, N′-cyclohexyl, N′, N′-diphenyl (in which case the two phenyl radicals may also be substituted or be linked with each other either directly or by means of a bridge member such, for example, as —CH₂—, —NH—, —O—, or —S —) N′-methyl-N′-phenyl-, N′,-N′-dicycohexyl-ureas as well as cyclohexyl-carbamoyl-imidazoles, -pyrazoles or -triazoles as well as compounds which carry, instead of cyclohexyl, another substituent within the range of the above definition of R¹.

The hydrolysis of the benzenesulfonyl-parabanic acids, benzenesulfonyl-isourea ethers, benzenesulfonyl isothiourea ethers or benzenesulfonyl-haloformic acid amidines mentioned as starting substances is suitably carried out in an alkaline medium. Isourea ethers may also be hydrolyzed successfully in an acid medium.

The replacement of the sulfur atom in the urea grouping of the correspondingly substituted benzenesulfonyl-thioureas by an oxygen atom can be effected in known manner, for example, with the aid of oxides or salts of heavy metals or with the use of oxidizing agents, such, for example, as hydrogen peroxide, sodium peroxide, nitrous acid or permanganates. The replacement of the sulfur atom in benzene-sulfonyl ureas and benzenesulfonylthioureas substituted by the group

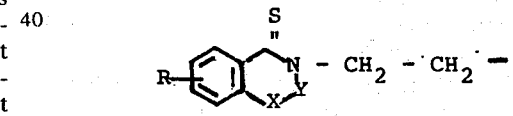

or the group

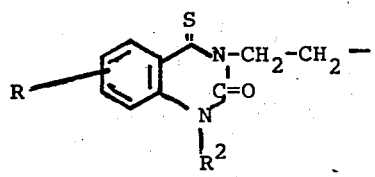

is advantageously carried out by means of oxidizing agents. The thioureas may also be desurphurized by treatment with phosgene or phosphorus pentachloride.

The chloroformic acid amidines or carbodiimides which can be obtained, for example, by desurphurization of the corresponding thioureas, may be converted into the benzenesulfonylureas by suitable measures such, for example, as by saponification or addition of water.

The manufacture of the benzenesulfonyl-ureas according to process (f) which may be carried out stepwise, can be effected, for example, in such a manner that 2-amino-benzamido-ethyl-benzenesulfonyl-ureas are prepared in usual manner, advantageously by means of 2-nitro-benzamido-ethyl-benzenesulfonyl-ureas, and thereupon the ring is closed in suitable manner, for example, by the reaction with chloroformic acid alkyl ester, phosgene, formic acid, formaldehyde or urea to yield the reaction products of the general formula. As regards the reaction conditions, the manner of carrying out the process of the invention may in general, be varied within wide limits, and can be adapted to each individual case. For example, the reactions may be carried out with the use of solvents or without solvents, at room temperature or at an elevated temperature.

Depending on the nature of the starting substances, one or the other of the aforesaid methods may, in some cases, provide a desired individual benzenesulfonyl-urea only in a small yield or may be inappropriate for its synthesis. In such comparatively rare cases, the expert will have no difficulty in synthesizing the desired product according to one of the other methods of the process described.

The benzenesulfonyl-urea derivatives of the invention are valuable medicaments which have strong and long-lasting hypoglycemic action.

The hypoglycemic action of the products of the invention can be ascertained by administering them in the form of the sodium salts to normally fed rabbits in a dose of 10 mg/kg of body weight and determining the blood sugar level according to the known method of Hagedorn-Jensen or by means of an autoanalyzer for a prolonged period of time.

The benzenesulfonyl-ureas of the present invention are preferably used for the manufacture of orally administrable pharmaceutical preparations for the lowering of the blood sugar level in the treatment of diabetes mellitus, and may be used as such or in the form of their physiologically tolerable salts or in the presence of substances which cause salt formation. For the formation of salts, there may be used, for example, alkaline agents such as alkali metal- or alkaline earth metal hydroxides and alkali metal or alkaline earth metal carbonates or bicarbonates.

The present invention also provides pharmaceutical preparations for oral administration and lowering the blood sugar level in the treatment of diabetes mellitus, which comprises a compound of the above general formula (1) or (1') or a physiologically tolerable salt thereof in admixture or conjunction with a pharmaceutically suitable carrier.

The pharmaceutical preparations of the invention are preferably in the form of tablets and as pharmaceutically suitable carriers there may be mentioned, for example, talc, starch, lactose, tragacanth and magnesium stearate.

A pharmaceutical preparation, for example, a tablet or a powder, containing a benzenesulfonyl-urea of the invention or a physiologically tolerable salt thereof as the active substance, with or without one or more of the aforementioned carriers, is advantageously brought into a suitable dosage unit form. The dose chosen should comply with the activity of the benzene-sulfonyl-urea used and with the desired effect. Advantageously, the dosage per unit amounts to about 5 to 500 mg, preferably 10 to 100 mg, but considerably higher or lower dosage units may also be used, which, when required, are divided or multiplied prior to their administration.

The following Examples illustrate the invention:

EXAMPLE 1

N-[4-($\beta$-3,4-dihydro-4-oxo-3-quinazolinyl-ethyl)-benzenesulfonyl]-N'-cyclohexyl-urea 16.5 g of 4-($\beta$-3,4-dihydro-4-4-oxo-3-quinazolinyl-ethyl)-benzenesulfonamide (m.p. 253° – 255°C, prepared from 4-($\beta$-2-aminobenzamido-ethyl)-benzenesulfonamide and formic acid) were dissolved in the solution of 2 g of sodium hydroxide in water and 200 ml of acetone. 6.5 of cyclohexyl-isocyanate were added dropwise while stirring and the solution was stirred for 2 hours. Water was added, the solution was filtered and acidified. The precipitate was suction-filtered, reprecipitated from 1% ammonia and recrystallized from ethanol-dimethyl-formamide. The N-[$\beta$-(3,4-dihydro-4-oxo-3-quinazolinyl ethyl)-benzenesulfonyl]-N'-cyclohexyl-urea melted at 227°–229°C.

In analogous manner there were obtained:
N-[4-(3,4-dihydro-4-oxo-3-quinazolinyl ethyl)-benzenesulfonyl]-N'-(4-methyl-cyclohexyl)-urea, m.p. 184°–186°C (from water-ethanol);
N-[4-($\beta$-3,4-dihydro-4-dihydro-4-oxo-3-quinazolinyl-ethyl)-benzenesulfonyl]-N'-butyl-urea, m.p. 221°–223°C (from ethanol);
N-[4-($\beta$-3,4-dihydro-4-oxo-3-quinazolinyl-ethyl)-benzenesulfonyl]-N'-(4-ethyl-cyclohexyl)-urea, m.p. 190°–192°C (from ethanol);

In analogous manner there were obtained from 4-($\beta$-6-chloro-3,4-dihydro-4-oxo-3-quinazolinyl-ethyl)-benzenesulfonamide, m.p. 248°–249°C:
N-[4-($\beta$-6-chloro-3,4-dihydro-4-oxo-3-quinazolinyl-ethyl)-benzenesulfonyl]-N'-cyclohexyl-urea, m.p. 225°–227°C (from ethanol);
N-[4-($\beta$-6-chloro-3,4-dihydro-4-oxo-3-quinazolinyl-ethyl)-benzenesulfonyl]-N'-(4-methylcyclohexyl)-urea, m.p. 219°–221°C (from ethanol);
N-[4-($\beta$-6-chloro-3,4-dihydro-4-oxo-3-quinazolinyl-ethyl)-benzenesulfonyl]-N'-butyl-urea, m.p. 237°–239°C (from ethanol-DMF);

In analogous manner there were obtained from 4-($\beta$-7-methyl-3,4-dihydro-4-oxo-3-quinazolinyl-ethyl)-benzenesulfonamide, m.p. 258°–260°C.
N-[4-($\beta$-7-methyl-3,4-dihydro-4-oxo-3-quinazolinyl-ethyl)-benzenesulfonyl]-N'-cyclohexyl-urea, m.p. 221°–223°C (from ethanol-DMF);
N-[4-($\beta$-7-methyl-3,4-dihydro-4-oxo-3-quinazolinyl-ethyl)-benzenesulfonyl]-N'-(4-methyl-cyclohexyl)-urea, m.p. 205°–207°C (from ethanol);
N-[4-($\beta$-7-methyl-3,4-dihydro-4-oxo-3-quinazolinyl-ethyl)-benzenesulfonyl]-N'-(4-ethylcyclohexyl)-urea, m.p. 204°–206°C (from ethanol);

In analogous manner there were obtained from 4-($\beta$-2-methyl-3,4-dihydro-4-oxo-3-quinazolinyl-ethyl)-benzenesulfonamide, m.p. 252°–245°C:
N-[4-($\beta$-2-methyl-3,4-dihydro-4-oxo-3-quinazolinyl-ethyl)-benzenesulfonyl]-N'-cyclohexyl-urea, m.p. 253°–254°C (from ethanol-DMF);

In analogous manner there were obtained from 4-($\beta$-2-ethyl-3,4-dihydro-4-oxo-3-quinazolinyl-ethyl)-benzenesulfonamide, m.p. 248°–250°C:
N-[4-($\beta$-2-ethyl-3,4-dihydro-4-oxo-3-quinazolinyl-ethyl)-benzenesulfonyl]-N'-cyclohexyl-urea, m.p. 216°–218°C (from ethanol-DMF);
N-[4-($\beta$-2-ethyl-3,4-dihydro-4-oxo-3-quinazolinyl-ethyl)-benzenesulfonyl]-N'-(4-methylcyclohexyl)-urea, m.p. 207°–209°C (from ethanol-DMF).

EXAMPLE 2

N-[4-(β-1,2,3,4-tetrahydro-4-oxo-3-quinazolinyl-ethyl)-benzenesulfonyl]-N'-cyclohexyl-urea 8.3 g of 4-(β-1,2,3,4-tetrahydro-4-oxo-3-quinazolinylethyl)-benzenesulfonamide (m.p. 219°–221°C, prepared from 4-(β-2-amino-benzamido-ethyl)-benzenesulfonamide and formaldehyde) were reacted in 100 ml of acetone, the solution of 1 g of NaOH in water and 3.3 g of cyclohexyl-isocyanate and worked up as described above. The N-[4-(β-1,2,3,4-tetrahydro-4-oxo-3-quinazolinyl-ethyl)-benzenesulfonyl]-N'-cyclohexyl-urea melted at 186°–188°C after recrystallization from water-ethanol.

In an analogous manner there were obtained
N-[4-(β-1,2,3,4-tetrahydro-4-oxo-3-quinazolinyl-ethyl)-benzenesulfonyl]-N'-butyl-urea, m.p. 188°–190°C (from water-ethanol);
N-[4-(β-1,2,3,4-tetrahydro-4-oxo-3-quinazolinyl-ethyl)-benzenesulfonyl]-N'-(4-methyl-cyclohexyl)-urea, m.p. 208°–210°C (from ethanol;

In an analogous manner there were obtained from 4-(β-7-methyl-1,2,3,4-tetrahydro-4-oxo-3-quinazolinyl-ethyl)-benzenesulfonamide:
N-[4-(β-7-methyl-1,2,3,4-tetrahydro-4-oxo-3-quinazolinyl-ethyl)-benzenesulfonyl]-N'-cyclohexyl-urea, m.p. 185°–187° (from ethanol);
N-[4-(β-7-methyl-1,2,3,4-tetrahydro-4-oxo-3-quinazolinyl-ethyl)-benzenesulfonyl]-N'-(4-methylcyclohexyl)-urea, m.p. 206°–208°C (from ethanol);
N-[4-(β-7-methyl-1,2,3,4-tetrahydro-4-oxo-3-quinazolinyl-ethyl)-benezenesulfonyl]-N'-(4-ethyl-cyclohexyl)-urea, m.p. 200°–202°C (from ethanol);

In an analogous manner there were obtained from 4-(β-6-chloro-1,2,3,4-tetrahydro-4-oxo-3-quinazolinyl-ethyl)-benzenesulfonamide, m.p. 208°–209°C:
N-[4-(β-6-chloro-1,2,3,4-tetrahydro-4-oxo-3-quinazolinyl-ethyl)-benzenesulfonyl]-N'-cyclohexyl-urea, m.p. 181°–183°C (from ethanol-DMF);
N-[4-(β-6-chloro-1,2,3,4-tetrahydro-4-oxo-3-quinazolinyl-ethyl)-benzenesulfonyl]-N'-(4-methylcyclohexyl)-urea, m.p. 190°–192°C (from ethanol);
N-[4-(β-6-chloro-1,2,3,4-tetrahydro-4-oxo-3-quinazolinyl-ethyl)-benzenesulfonyl]-N'-butyl-urea, m.p. 182°–184°C (from ethanol);

In an analogous manner there were obtained from 4-(β-6-chloro-2,2-dimethyl-1,2,3,4-tetrahydro-4-oxo-3-quinazolinyl-ethyl)-benzenesulfonamide, m.p. 234°–235°C:
N-[4-(β-6-chloro-2,2-dimethyl-1,2,3,4-tetrahydro-4-oxo-3-quinazolinyl-ethyl)-benzenesulfonyl]-N'-(4-methylcyclohexyl)-urea, m.p. 200°–201°C (from methanol-DMF);

EXAMPLE 3

N-[4-(β-1,2,3,4-tetrahydro-2,4-dioxo-3-quinazolinyl-ethyl)-benzenesulfonyl]-N'-cyclohexyl-urea 8.65 g of 4-(β-1,2,3,4-tetrahydro-2,4-dioxo-3-quinazolinylethyl)-benzenesulfonamide, m.p. 307°–311°C, (prepared by melting together 4-(β-2-amino-benzamidoethyl)-benzenesulfonamide and urea) were dissolved in 100 ml of acetone, 1 g of sodium hydroxide and water, 3.3 g of cyclohexyl-isocyanate were added dropwise at room temperature while stirring, and stirring was continued for 2 hours at room temperature. Then, the solution was diluted with water, filtered and the filtrate was acidified. The precipitated N-[4-(β-1,2,3,4-tetrahydro-2,4-dioxo-3-quinazolinyl-ethyl)-benzenesulfonyl]-N'-cyclohexyl-urea was recrystallized from ethanol-DMF and melted at 250°C.

In an analogous manner there was obtained
N-[4-(β-1,2,3,4-tetrahydro-2,4-dioxo-3-quinazolinyl-ethyl)-benzenesulfonyl]-N'-butyl-urea, m.p. 230°C (from ethanol-DMF);
N-[4-(β-1,2,3,4-tetrahydro-2,4-dioxo-3-quinazolinyl-ethyl)-benzenesulfonyl]-N'-(4-methylcyclohexyl)-urea, m.p. 245°C (from ethanol);
N-[4-(β-1,2,3,4-tetrahydro-2,4-dioxo-3-quinazolinyl-ethyl)-benzenesulfonyl]-N'-(2,5-endoethylene-cyclohexyl)-urea, m.p. 232°–234°C (from methyl-dioxane);
N-[4-(β-1,2,3,4-tetrahydro-2,4-dioxo-3-quinazolinyl-ethyl)-benzenesulfonyl]-N'-(4-chlorocyclohexyl)-urea, m.p. 225°–227°C (from methanol-dioxane);
N-[4-(β-1,2,3,4-tetrahydro-2,4-dioxo-3-quinazolinyl-ethyl)-benzenesulfonyl]-N'-$\Delta^3$-cyclohexenyl-urea, m.p. 206°–208°C (from methanol dioxane);
N-[4-(β-1,2,3,4-tetrahydro-2,4-dioxo-3-quinazolinyl-ethyl)-benzenesulfonyl]-N'-cyclopentyl-urea, m.p. 229°–231°C (from methanol-dioxane);

In an analogous manner there were obtained from 4-(β-7-methyl-1,2,3,4-tetrahydro-2,4-dioxo-3-quinazolinyl-ethyl)-benzenesulfonamide, m.p. 303°–304°C:
N-[4-(β-7-methyl-1,2,3,4-tetrahydro-2,4-dioxo-3-quinazolinylethyl)-benzenesulfonyl]-N'-cyclohexyl-urea, m.p. 313°–314°C (from ethanol-DMF)
N-[4-(β7-methyl-1,2,3,4-tetrahydro-2,4-dioxo-3-quinazolinylethyl)-benzenesulfonyl]-N'-(4-methylcyclohexyl)-urea, m.p. 260°C (from ethanol-DMF);

In an analogous manner there was obtained from 4-(β-6-chloro-1,2,3,4-tetrahydro-2,4-dioxo-3-quinazolinylethyl)-benzenesulfonamide, m.p. 307°–309°C:
N-[4-(β-6-chloro-1,2,3,4-tetrahydro-2,4-dioxo-3-quinazolinylethyl)-benzenesulfonyl]-N'-cyclohexyl-urea, m.p. 250°C (from ethanol-DMF);

EXAMPLE 4

N-[4-(β-3,4-dihydro-4-oxo-1,2,3-benzo[e]-triazine-3-yl-ethyl)-benzenesulfonyl]-N'-cyclohexyl-urea 8.25 g of 4-(β-3,4-dihydro-4-oxo-1,2,3,-benzo[e]-triazine-3-yl-ethyl)-benzenesulfonamide (m.p. 232°–234°C, prepared from 4-(β-2-aminobenzamidoethyl)-benzenesulfonamide and nitrous acid) were boiled under reflux in 200 ml of acetone with 10 g of potassium carbonate and 3.3 g of cyclohexylisocyanate while stirring. The solution was suction-filtered after cooling, dissolved in water, filtered and the filtrate was acidified. The precipitated N-[4-(β-3,4-dihydro-4-oxo-1,2,3-benzo[e]-triazine-3-yl-ethyl)-benzenesulfonyl]-N'-cyclohexyl-urea melted at 213°–215°C after recrystallization from ethanol.

In an analogous manner there were obtained N-[4-(β-3,4-dihydro-4-oxo-1,2,3-benzo[e]-triazine-3-yl-ethyl)-benzenesulfonyl]-N'-(4-methylcyclohexyl)-urea, m.p. 212°–214°C (from ethanol);

N-[4-(β-3,4-dihydro-4-oxo-1,2,3-benzo[e]-triazine-3-yl-ethyl)-benzenesulfonyl]-N'-butyl-urea, m.p. 211°–213°C (from ethanol);

EXAMPLE 5

N-[4-(β-2H-4H-2,3-dioxo-1,3-benzoxazine-3-yl-ethyl)-benzenesulfonyl]-N'-(4-methylcyclohexyl)-urea 7.5 g of 4-(β-2H, 4H-2,4-dioxo-1,3-benzoxazine-3-yl-ethyl)-benzenesulfonamide (m.p. 266°–267°) were boiled for 3 hours in 250 ml of acetone with 6 g of ground potassium carbonate. Then, 3.2 g of trans-4-methylcyclohexyl-isocyanate were added and the whole was boiled for 8 hours while stirring. After cooling, the solution was suction-filtered, the precipitate was introduced in water and acidified. The precipitated product was recrystallized from methanol-DMF. The obtained N-[4-(β-2H, 4H-2,4-dioxo-1,3-benzaoxazine-3-yl-ethyl)-benzenesulfonyl]-N'-(4-methyl-cyclohexyl)-urea melted at 220°–221°C.

In an analogous manner of in accordance with Example 1 there was obtained

N-[4-(β-2H, 4H-2,4-dioxo-1,3-benzoxazine-3-yl-ethyl)-benzenesulfonyl]-N'-cyclohexyl-urea, m.p. 227°–228°C (from methanol-DMF);

In an analogous manner there were obtained from
4-(β-6-methyl-2H, 4H-2,4-dioxo-1,3-benzoxazine-3-yl-ethyl)-benzenesulfonamide, m.p. 242°–243°C:

N-[4-(β-6-methyl-2H, 4H-2,4-dioxo-1,3-benzoxazine-3-yl-ethyl)-benzenesulfonyl]-N'-cyclohexyl-urea, m.p. 218°–220°C (from methanol-DMF);

N-[4-(β-6-methyl-2H, 4H2,4-dioxo-1,3-benzoxazine-3-yl-ethyl)-benzenesuslfonyl]-N'-(4-methyl-cyclohexyl)-urea, m.p. 222°–223°C (from methanol-DMF);

N-[4-(β-6-methyl-2H, 4H-2,4-dioxo-1,3-benzoxazine-3-yl-ethyl)-benzenesulfonyl]-N'-butyl-urea, m.p. 200°–201°C (from methanol-DMF);

from 4-(β-6-chloro-2H, 4H-2,4-dioxo-1,3-benzoxazine-3-yl-ethyl)-benzenesulfonamide, m.p. 259°–261°C:

N-[4-(β-6-chloro-2H, 4H-2,4-dioxo-1,3-benzoxazine-3-yl-ethyl)-benzenesulfonyl]-N'-cyclohexyl-urea, m.p. 221°–223°C (from methanol-DMF);

N-[4-(β-6-chloro-2H, 4H-2,4-dioxo-1,3-benzoxazine-3-yl-ethyl)-benzenesulfonyl]-N'-(4-methyl-cyclohexyl)-urea, m.p. 235°–237°C (from methanol);

from 4-(β-6-methoxy-2H, 4H-2,4-dioxo-1,3-benzoxazine-3-yl-ethyl)-benzenesulfonamide, m.p. 245°–247°C:

N-[4-(β-6-methoxy-2H, 4H-2,4-dioxo-1,3-benzoxazine-3-yl-ethyl)-benzenesulfonyl]-N'-cyclohexyl-urea, m.p. 194°–196°C;

N-[4-(β-6-methoxy-2H, 4H-2,4-dioxo-1,3-benzoxazine-3-yl-ethyl)-benzenesulfonyl]-N'-(4-methyl-cyclohexyl)-urea, m.p. 205°C (from methanol-DMF);

EXAMPLE 6

N-[4-(β-3,4-dihydro-4-oxo-3-quinazolinyl-ethyl)-benzenesulfonyl]-N'-cyclohexyl-urea 4.6 g of N-[4-(β-3,4-dihydro-4-oxo-3-quinazolinylethyl)-benzenesulfonyl]-N'-cyclohexyl-thiourea (m.p. 194°–195°C, prepared by the reaction of 4-(β-3,4-dihydro-4-oxo-3-quinazolinyl-ethyl)-benzenesulfonamide with cyclohexyl-isothiocyanate) were dissolved in 250 ml of methanol and boiled under reflux for 4 hours after the addition of 2.1 g of mercury oxide and a small amount of potassium carbonate while stirring. The mercury sulfide was suction-filtered and the solvent was eliminated in vacuo. The N-[4-(β-3,4-dihydro-4-oxo-3-quinazolinyl-ethyl)-benzenesulfonyl]-N'-cyclohexyl-iso-urea-methyl ether thus obtained was recrystallized from water-methanol and melted at 107°–109°C.

0.2 g of N-[4-(β-3,4-dihydro-4-oxo-3-quinazolinyl-ethyl)-benzenesulfonyl]-N'-cyclohexyl-isourea-methyl ether were heated for 3 minutes on the steam bath in 30 ml of concentrated hydrochloric acid. The crystals which formed were suction-filtered after cooling, washed with water and recrystallized from water-methanol-dioxan. The N-[4-(β-3,4-dihydro-4-oxo-3-quinazolinyl-ethyl)-benzenesulfonyl]-N'-cyclohexyl-urea obtained had a melting point of 228°–230°C.

EXAMPLE 7

N-[4-(β-3,4-dihydro-4-oxo-3-quinazolinyl-ethyl)-benzenesulfonyl]-N'-cyclohexyl-urea 2.0 g of N-[4-(β-3,4-dihydro-4-oxo-3-quinazolinyl-ethyl)-benzenesulfonyl]-N'-cyclohexyl-thiourea were suspended in 40 ml of 2N NaOH. After the addition of 10 ml of a 35% hydrogen peroxide solution the mixture was heated for 90 minutes on the steam bath. It was acidified with 2N hydrochloric acid and the crystals were suction-filtered. The N-[4-(β-3,4-dihydro-4-oxo-3-quinazolinyl-ethyl)-benzenesulfonyl]-N'-cyclohexyl-urea thus obtained melted at 227°–229°C after recrystallization from methanol-dioxan.

EXAMPLE 8

N-[4-(β-3,4-dihydro-4-oxo-3-quinazolinyl-ethyl)-benzenesulfonyl]-N'-cyclohexyl-urea 4.6 g of N-[4-(β-3,4-dihydro-4-oxo-3-quinazolinyl-ethyl)-benzenesulfonyl]-N'-cyclohexyl-thiourea and 2.06 g of dicyclohexyl-carbodiimide were dissolved in absolute dioxan. After having been allowed to stand for several days the N,N'-dicyclohexyl-thiourea formed (m.p. 176°–178°C) was suction-filtered and the filtrate concentrated in vacuo. The N-[4-(β-3,4-dihydro-4-oxo-3-quinazolinyl-ethyl)-benzenesulfonyl]-N'-cyclohexyl-carbodiimide was obtained as viscous residue which was reacted without further purification.

4.0 g of the sulfonyl-carbodiimide thus obtained were dissolved in dioxan and heated for 30 minutes on the steam bath after the addition of 10 ml of water. The reaction solution was introduced in a strongly dilute ammonia solution, filtered and acidified. The N-[4-(β-3,4-dihydro-4-oxo-3-quinazolinylethyl)-benzenesulfonyl]-N'-cyclohexyl-urea thus prepared was recrystallized from methanol-dioxan and melted at 227°–229°C.

EXAMPLE 9

N-[4-(β-1,2,3,4-tetrahydro-2,4-dioxo-3-quinazolinyl-ethyl)-benzenesulfonyl]-N'-(3-methylcyclopentyl)-urea 4.0 g of N-[4-(β-1,2,3,4-tetrahydro-2,4-dioxo-3-quinazolinyl-ethyl)-benzenesulfonyl]-carbamic acid methyl ester (m.p. 220°–222°C, prepared from 4-(β-1,2,3,4-tetrahydro-2,4-dioxo-3-quinazolinyl-ethyl)-benzenesulfonamide and chloroformic acid methyl ester in dioxan in the presence of potassium carbonate) were boiled for 1 hour under reflux with 1.4 g of 3-methylcyclo-pentyl-amine-hydrochloride and 1.0 g of triethylamine in 100 ml of dioxane. The solution was led into dilute hydrochloric acid and then N-[4-(β-1,2,3,4-tetrahydro-2,4-dioxo-3-quinazolinyl-ethyl)-benzenesulfonyl]-N'-(3-methylcyclopentyl)-urea thus obtained was recrystallized from methanol-dioxane after it had been dissolved and precipitated again. It had a m.p. of 231°–233°C.

The following further Examples illustrate the invention of the compounds of the formula 1' above.

EXAMPLE 10

N-[4-(β-1-methyl-1,2,3,4-tetrahydro2,4-dioxo-3-quinazolinyl-ethyl)-benzenesulfonyl]-N'-cyclohexyl-urea 15.1 g of 2-methylamino-benzoic acid were dissolved in 400 ml of tetrahydrofuran and cooled to 0°C after adding 40 g of triethylamine. 22.8 g of chloroformic acid methyl ester were added dropwise while stirring and the suspension thus obtained was stirred fr 1 hour at 0°C. Then, 24.8 g of 4-(β aminoethyl)-benzenesulfonamide-hydrochloride were introduced portionwise and stirring was continued for another 4 hours at room temperature. At a temperature of from 50° to 60°C, the solvent was eliminated in vacuo and the remaining residue was dissolved in dilute sodium hydroxide solution. The solution filtered with charcoal was acidified and the 4-(β-1-methyl-1,2,3,4-tetrahydro-2,4-dioxo-3-quinazolinyl-ethyl)-benzenesulfonamide which precipitated was recrystallized from methanol-dioxan-DMF. Melting point: 242°–244°C.

6.0 of 4-(β-1-methyl-1,2,3,4-tetrahydro-2,4-dioxo-3-quinazolinyl-ethyl-benzenesulfonamide were suspended in 50 ml of acetone and 50 ml of dioxane. 4.7 g of anhydrous potassium carbonate were added and the solution was stirred under reflux for 2 hours. Then, 2.2 g of cyclohexylisocyanate were added dropwise and the solution was stirred for 7 hours under reflux. The cooled suspension was concentrated to a large extent and the residue was dissolved in water. After filtration the solution was acidified and the N-[4-(β-1-methyl-1,2,3,4-tetrahydro-2,4-dioxo-3-quinazolinyl-ethyl)-benzenesulfonyl]-N'-cyclohexyl-urea was obtained which melted at 196°–197°C.

In an analogous manner there were obtained
N-[4-(β-1-methyl-1,2,3,4-tetrahydro-2,4-dioxo-3-quinazolinyl-ethyl)-benzenesulfonyl]-N'-butyl-urea, m.p. 177°C (from methanol-dioxan-water);
N-[4-(β-1-methyl-1,2,3,4-tetrahydro-2,4-dioxo-3-quinazolinyl-ethyl)-benzenesulfonyl]-N'-(4-methylcyclohexyl)-urea, m.p. 195°–196°C (from methanol-water);

In an analogous manner there were obtained from
4-(β-6-chloro-1-methyl-1,2,3,4-tetrahydro-2,4-dioxo-3-quinazolinyl-ethyl)benzenesulfonamide, m.p. 259°–260°C (from water-methanol-DMF):
N-[4-(β-6-chloro-1-methyl-1,2,3,4-tetrahydro-2,4-dioxo-3-quinazolinyl-ethyl)-benzenesulfonyl]-N'-cyclohexyl-urea, m.p. 210°–211°C (from methanol-DMF);
N-[4-(β-6-chloro-1-methyl-1,2,3,4-tetrahydro-2,4-dioxo-3-quinazolinyl-ethyl)-benzenesulfonyl]-N'-(4-methylcyclohexyl)urea, m.p. 214°–215°C (from methanol-DMF);
N-[4-(β-6-chloro-1-methyl-1,2,3,4-tetrahydro-2,4-dioxo-3-quinazolinyl-ethyl)-benzenesulfonyl]-N'-butyl-urea, m.p. 179°–180°C (from methanol-DMF);

In an analogous manner there were obtained from
4-(β-1-ethyl-1,2,3,4-tetrahydro-2,4-dioxo-3-quinazolinyl-ethyl)benzenesulfonamide, m.p. 224°–225°C (from water-ethanol);
N-[4-(β-1-ethyl-1,2,3,4-tetrahydro-2,4-dioxo-3-quinazolinylethyl)-benzenesulfonyl]-N'-cyclohexyl-urea, m.p. 204°–205°C (from methanol-dioxan);
N-[4-(β-1-ethyl-1,2,3,4-tetrahydro-2,4-dioxo-3-quinazolinylethyl)benzenesulfonyl-N'-(4-methylcyclohexyl)-urea, m.p. 204°–206°C (from water-methanol);
N-[4-(β-1-ethyl-1,2,3,4-tetrahydro-2,4-dioxo-3-quinazolinylethyl)-benzenesulfonyl]-N'-butyl-urea, m.p. 197°–198°C (from methanol-dioxan-water);
N-[4-(β-1-ethyl-1,2,3,4-tetrahydro-2,4-dioxo-3-quinazolinylethyl)-benzenesulfonyl]-N'-$\Delta^3$-cyclohexenyl-urea, m.p. 200°–201°C (from methanol-dioxan);
N-[4-(β-1-ethyl-1,2,3,4-tetrahydro-2,4-dioxo-3-quinazolinylethyl)-benzenesulfonyl]-N'-(4-ethyl-cyclohexyl)-urea, m.p. 196°–197°C (from methanol-dioxan);
N-[4-(β-1-ethyl-1,2,3,4-tetrahydro-2,4-dioxo-3-quinazolinylethyl)-benzenesulfonyl]-N'-cycloheptyl-urea, m.p. 192°–193°C (from methanol-dioxan);

In an analogous manner there were obtained from
4-(β-1-ethyl-6-chloro-1,2,3,4-tetrahydro-2,4-dioxo-3-quinazolinyl-ethyl)-benzenesulfonamide, m.p. 244°–245°C (from methanol-DMF):
N-[4-(β-1-ethyl-6-chloro-1,2,3,4-tetrahydro-2,4-dioxo-3-quinazolinyl-ethyl)-benzenesulfonyl]-N'-cyclohexyl-urea, m.p. 215°–216°C (from methanol-dioxan-water);
N-[4-(β-1-ethyl-6-chloro-1,2,3,4-tetrahydro-2,4-dioxo-3-quinazolinyl-ethyl)-benzenesulfonyl]-N'-(4-methylcyclohexyl)urea, m.p. m.p. 206°–207°C (from methanol-dioxan-water);
N-[4-(β-1-ethyl-6-chloro-1,2,3,4-tetrahydro-2,4-dioxo-3-quinazolinyl-ethyl)-benzenesulfonyl]-N'-butyl-urea, m.p. 197°–198°C (from methanol-dioxan-water.

In a analogous manner there were obtained from
4-(β-1-butyl-1,2,3,4-tetrahydro-2,4-dioxo-3-quinazolinyl-ethyl)-benzenesulfonamide, m.p. 201°C (from methanol-dioxane):
N-[4-(β-1-butyl-1,2,3,4-tetrahydro-2,4-dioxo-3-quinazolinylethyl)-benzenesulfonyl]-N'-cyclohexyl-urea, m.p. 215°–216°C (from methanol-dioxan);
N-[4-(β-1-butyl-1,2,3,4-tetrahydro-2,4-dioxo-3-quinazolinylethyl)-benzenesulfonyl]-N'-(4-methylcyclohexyl)-urea, m.p. 211°–212°C (from methanol-dioxan);
N-[4-('-1-butyl-1,2,3,4-tetrahydro-2,4-dioxo-3-quinazolinylethyl)-benzenesulfonyl]-N'-butyl-urea, m.p. 167°–168°C (from methanol-dioxan);

In an analogous manner there were obtained from
4-(β-1-butyl-6-chloro-1,2,3,4-tetrahydro-2,4-dioxo-3-quinazolinyl-ethyl)-benzenesulfonamide, m.p. 208°–210°C (from methanol-dioxan):
N-[4-(β-1-butyl-6-chloro-1,2,3,4-tetrahydro-2,4-dioxo-3-quinazolinyl-ethyl)-benzenesulfonyl]-N'-cycloheptyl-urea, m.p. 186°–187°C (from methanol-dioxan);
N-[4-(β-1-butyl-6-chloro-1,2,3,4-tetrahydro-2,4-dioxo-3-quinazolinyl-ethyl)-benzenesulfonyl]-N'-

Δ³-cyclohexenyl-urea m.p. 206°–207°C (from methanol-dioxan);

N-[4-(β-1-butyl-6-chloro-1,2,3,4-tetrahydro-2,4-dioxo-3-quinazolinyl-ethyl)-benzenesulfonyl]-N'-cyclohexyl-urea, m.p. 206°–208°C (from methanol-dioxan-water);

N-[4-(β-1-butyl-6-chloro-1,2,3,4-tetrahydro-2,4-dioxo-3-quinazolinyl-ethyl)-benzenesulfonyl]-N'-butyl-urea, m.p. 180°–182°C (from methanol-dioxan-water).

The following Table shows the hydpoglycemic action of some compounds of the invention and previously exemplified.

TABLE

| Compound | Lowering of the blood sugar level of rabbits after oral administration of 10 mg/kg after | | | |
|---|---|---|---|---|
| | 1 | 3 | 6 | 24 hours |
| N-[4-(β-1-ethyl-1,2,3,4-tetrahydro-2,4-dioxo-3-quinazolinyl-ethyl)-benzenesulfonyl]-N'-cyclohexyl-urea | 35 | 41 | 36 | 12 |
| N-[4-(β-1-ethyl-6-chloro-1,2,3,4-tetrahydro-2,4-dioxo-3-quinazolinyl-ethyl)-benzenesulfonyl]-N'-n-butyl-urea | 24 | 27 | 31 | 15 |
| N-[4-(β-1-ethyl-6-chloro-1,2,3,4-tetrahydro-2,4-dioxo-3-quinazolinyl-ethyl)-benzenesulfonyl]-N'-cyclohexyl-urea | 33 | 42 | 39 | 13 |
| N-[4-(β-6-chloro-1-methyl-1,2,3,4-tetrahydro-2,4-dioxo-3-quinazolinyl-ethyl)-benzenesulfonyl]-N'-n-butyl-urea | 10 | 21 | 23 | 14 |
| N-[4-(β-ethyl)-1,2,3,4-tetrahydro-2,4-dioxo-3-quinazolinyl-ethyl)-benzenesulfonyl]-N'-(4-methyl-cyclohexyl)-urea | 30 | 29 | 27 | 14 |

We claim:
1. A benzenesulfonyl urea of the formula

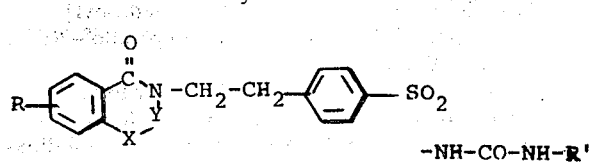

-NH-CO-NH-R' in which
R represents a hydrogen, chlorine, or bromine atom, a methoxy or methyl group,
—X—Y— represents —N=CH—, —NH—CH₂—, —NH—CO—,

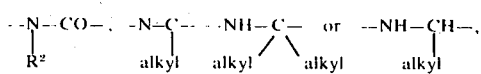

the alkyl herein containing from 1 to 4 carbon atoms,
R² represents an alkyl group having from 1 to 4 carbon atoms,
R' represents an alkyl group having from 3 to 6 carbon atoms, a cycloalkyl group having from 5 to 8 carbon atoms, 3-ethylcyclopentyl, methyl-cyclopentyl, dimethylcyclopentyl, 4-alkylcyclohexyl having from 1 to 3 carbon atoms in the alkyl group, cyclopentenyl, cyclohexenyl, cycloheptenyl, 4-chloro-cyclohexyl, 4,4-dimethylcyclohexyl, 3-methylcyclopentenyl, 4-methylcyclohexenyl; endoalkylene-cyclohexyl, endoalkylene-cyclohexenyl, each having 1 to 2 endoalkylene carbon atoms; bicyclo-(2.2.1) hept-2-2n-7-yl, or the physiologically tolerable salts thereof.

2. A benzenesulfonyl urea of the formula

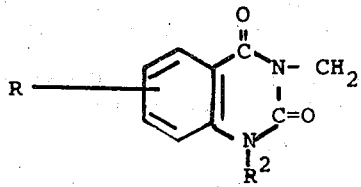

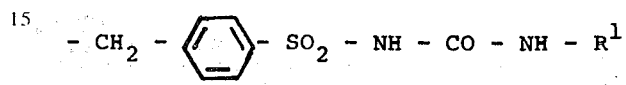

in which
R represents a hydrogen, chlorine, or bromine atom or a methoxy or methyl group,
R' represents an alkyl group having from 3 to 6 carbon atoms, a cycloalkyl group having from 5 to 8 carbon atoms, 3-ethylcyclopentyl, methyl-cyclopentyl, dimethylcyclopentyl, 4-alkylcyclohexyl having from 1 to 3 carbon atoms in the alkyl group, cyclopentenyl, cyclohexenyl, cycloheptenyl, 4-chloro-cyclohexyl, 4,4-dimethylcyclohexyl, 3-methylcyclopentenyl, 4-methylcyclohexenyl, bicyclo-(2.2.1) hept-2-en-7-yl, endoalkylene-cyclohexyl, endoalkylene-cyclohexenyl, having 1 or 2 endoalkylene-carbon atoms each,
R² represents an alkyl group having from 1 to 4 carbon atoms or the physiologically tolerable salts thereof.

3. The compound as defined in claim 2, wherein the R' moiety is an endoalkylene-cyclohexyl or endoalkylene-cyclohexenyl which has 1 or 2 endoalkylene carbon atoms in said endoalkylene moiety.

4. A benzenesulfonyl urea of the formula

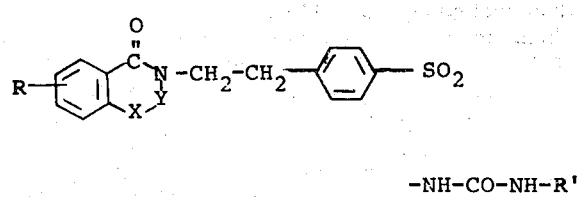

-NH-CO-NH-R' in which
R represents a hydrogen, chlorine, or bromine atom, a methoxy or methyl group,
—X—Y— represents —N=CH—, —NH—CH₂—, —NH—CO—, N=C,
                                              |
                                             akyl

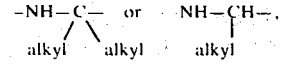

the alkyl herein containing from 1 to 4 carbon atoms,
R' represents an alkyl group having from 3 to 6 carbon atoms, a cycloalkyl group having from 5 to 8 carbon atoms, 3-ethylcyclopentyl, methyl-cyclopentyl, dimethylcyclopentyl, 4-alkylcyclohexyl having from 1 to 3 carbon atoms in the alkyl group, cyclopentenyl, cyclohexenyl, cycloheptenyl, 4-chloro-cyclohexyl, 4,4-dimethylcyclohexyl, 3-methylcyclopentenyl, 4-methylcyclohexenyl; endoalkylene-cyclohexyl, endoalkylene-cyclohexenyl, each having 1 or 2 endoalkylene carbon atoms; bycyclo-(2.2.1) hept-2-2n-7-yl, or the physiologically tolerable salts thereof.

5. The compound as defined in claim 1 which is N-[4-($\beta$-1,2,3,4-tetrahydro-2,4-dioxo-3-quinazolinyl-ethyl)-benzenesulfonyl]-N'-cyclohexyl-urea.

6. The compound as defined in claim 1 which is N-[4-($\beta$-3,4-dihydro-4-oxo-3-quinazolinyl-ethyl)-benzenesulfonyl]N'-(4-methyl-cyclohexyl)-urea.

7. The compound as defined in claim 1 which is N-[4-($\beta$-6-chloro-1,2,3,4-tetrahydro-4-oxo-3-quinazolinyl-ethyl)-benzenesulfonyl]-N'-cyclohexyl-urea 8. The compound as defined in claim 1 which is N-[4-($\beta$-7-methyl-1,2,3,4-tetrahydro-4-oxo-3-quinazolinyl-ethyl)-benzenesulfonyl]-N'-(4-methyl-cyclohexyl)urea.

9. The compound as defined in claim 1 which is N-[4-($\beta$-6-chloro-1-methyl-1,2,3,4-tetrahydro-2,4-dioxo-3-quinazolinyl-ethyl)-benzenesulfonyl]-N'-cyclohexyl-urea.

10. The compound as defined in claim 1 which is N-[4-($\beta$-1-ethyl-1,2,3,4-tetrahydro-2,4-dioxo-3-quinazolinyl-ethyl)-benzenesulfonyl]-N'-cyclohexyl-urea.

11. The compound as defined in claim 1 which is N-[4-($\beta$-1-ethyl-1,2,3,4-tetrahydro-2,4-dioxo-3-quinazolinyl-ethyl)-benzenesulfonyl]-N'-(4-methyl-cyclohexyl)urea.

12. The compound as defined in claim 1 which is N-[4-($\beta$-1-ethyl-6-chloro-1,2,3,4-tetrahydro-2,4-dioxo-3-quinazolinyl-ethyl)-benzenesulfonyl]-N'-cyclohexyl-urea.

13. The compound as defined in claim 1 which is N-[4-($\beta$-1-ethyl-6-chloro-1,2,3,4-tetrahydro-3,4-dioxo-3-quinazolinyl-ethyl)-benzenesulfonyl]-N'-butyl-urea.

* * * * *